Dec. 15, 1964 E. SCHWARTZ Plant Pat. 2,463
ROSE PLANT
Filed Oct. 18, 1963
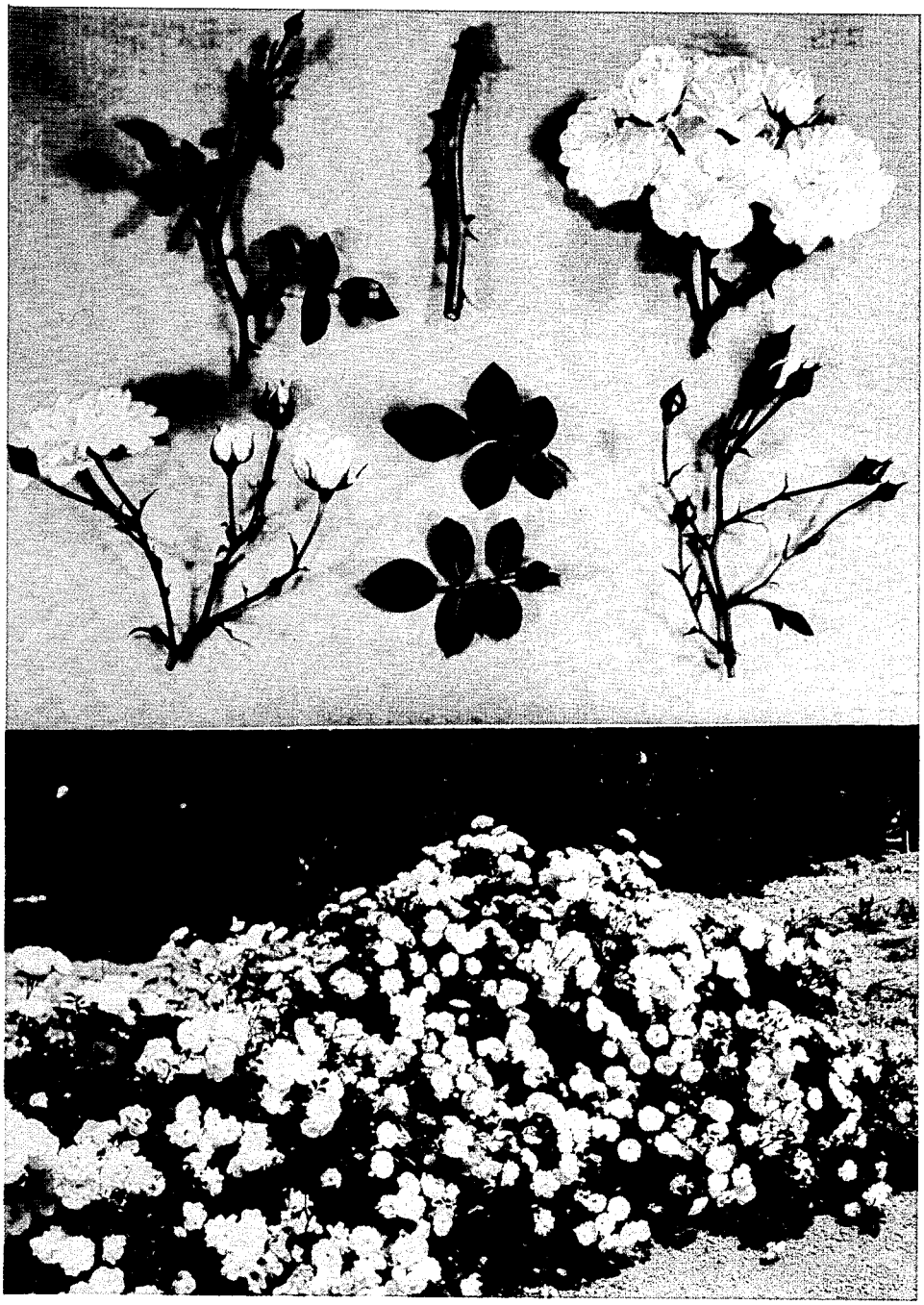
Inventor.
Ernest Schwartz
By: Robb & Robb
Attorneys.

United States Patent Office

Plant Pat. 2,463
Patented Dec. 15, 1964

2,463
ROSE PLANT

Ernest Schwartz, Kingsville, Md., assignor to The Conard-Pyle Company, West Grove, Pa., a corporation of Pennsylvania Filed Oct. 18, 1963, Ser. No. 317,393
1 Claim. (Cl. Plt.—1)

The present invention relates to a new and distinct variety of rose plant of the shrub class, which was originated by me by crossing the variety "White Dawn" (unpatented) with the variety "Pinocchio" (Plant Patent No. 484).

As the result of this breeding, I have produced a new and improved rose variety which is endowed with the following outstanding characteristics which distinguish the same from its parents, as well as from all other varieties of which I am aware:

(1) A compact and bushy habit of growth, with a gradually spreading habit which makes the plant equally suitable for hedge or ground cover purposes;

(2) Glossy, disease resistant foliage, which makes the plant especially valuable for maintenance free plantings;

(3) Outstandingly good floriferousness and continuity of flowering;

(4) A habit of bearing the flowers in clusters;

(5) A distinctive and attractive white flower color;

(6) A slight, spicy flower fragrance; and (7) A winter hardiness which is superior to the average rose variety grown in West Grove, Pennsylvania.

In comparison with its seed parent "White Dawn," the new variety produces a more compact bush, with more foliage; it produces more blooms than this parent by reason of the fact that all of the flowers are borne on the current year's wood; while the flowers are not as large as those of this parent, they occur in greater number in each cluster; and the new variety is superior in resistance to mildew and blackspot.

As compared with the pollen parent "Pinocchio", the new variety grows in a form suitable for either a ground cover or a shrub, as distinguished from the floribunda habit of this parent; it is more floriferous; the flowers are white in color, as distinguished from those of "Pinocchio" which have a pink tint or blend; and the new variety is endowed with superior winter hardiness.

Asexual reproduction of my new variety by budding shows that the foregoing characteristics and distinctions come true to form and are established and transmitted through succeeding propagations.

The acompanying drawing shows typical specimens of the vegetative growth and flowers of my new variety in different stages of development, as well as a typical blooming hedge planting illustrative of the spreading habit of growth, all as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor; seedling; for garden decoration.

Class: Shrub.

Breeding: Seedling.

*Seed parent.*—"White Dawn."

*Pollen parent.*—"Pinocchio."

Propagation: Holds its distinguishing characteristics through succeeding propagations by budding.

*Flower*

Locality where grown and observed: West Grove, Pennsylvania.

Flowers borne: Several to stem; in regular clusters; on stems of medium length and normal strength.

Quantity of bloom: Abundant; outdoors.

Continuity: Continuous.

Fragrance: Slight. Nature—spicy.

Bud:

*Peduncle.*—Short; slender; erect; stiff; rough; with medium number of gland tipped red hairs. Color—reddish.

*Before calyx breaks.*—Size—small. Form—short; pointed; globular; with a conspicuous neck; with foliaceous appendages on the surface of the bud; with little bristle-like foliaceous parts extending beyond the tip of the bud equal to less than ¼ of its length.

*As calyx breaks.*—Color—white, with irregular markings of Lettuce Green, Plate 861.

*As first petal opens.*—Size—small. Form—short; pointed-ovoid. Color: outside—white, thinly and lightly veined with Pod Green, Plate 061; inside—white, lightly veined with Pod Green, Plate 061.

*Opening.*—Opens up well.

Bloom:

*Size (when fully open).*—From small to medium; from 2¼ to 2½ inches.

*Petalage.*—Very double; from 60 to 70 petals; arranged irregularly.

*Form.*—High-centered at first, but becoming cupped; petals at first being from flat to slightly rolled outward, but later becoming loosely rolled outward at maturity.

Petals:

*Texture.*—Thin.

*Appearance.*—Inside—satiny. Outside—satiny.

*Shape.*—Outer petals—obovate; scalloped; with base flat. Intermediate petals—lanceolate; generally with one notch. Inner petals—usually with one or more notches.

This description of a newly opened flower was made from a rose grown outdoors during the month of August, at West Grove, Pennsylvania:

*Color.*—Outer petal: outside surface—white; inside surface—white. Intermediate petal: outside surface—white; inside surface—white. Inner petal: outside surface—white; inside surface—white.

This description was made of a rose grown outdoors that was open for three days during the month of August, at West Grove, Pennsylvania:

*Color.*—Outer petal: outside surface—white; inside surface—white. Inner petal: outside surface—white; inside surface—white.

*General color effect.*—Newly opened flower—white, with slight pink tones in the center of the bloom but which are not apparent when the individual petals are examined. Three days open—white.

*Behavior.*—Drop off cleanly.

*Flower longevity.*—On bush in garden—three days during August. Cut roses grown outdoors and kept at living room temperatures—three days during August.

*Reproductive Organs*

Stamens: Very few; arranged irregularly about pistils; mixed with petaloids; tucked in receptacle.

Filaments: Many; short; most with anthers. Color—white.

Anthers: Open at various times; small; seldom an anther fused with a petaloid. Color—yellow.
Pollen: Sparse. Color—gold.
Pistils: From few to medium number.
Styles: Even; short; thin; bunched.
Stigma: Color—yellow.
Ovaries: All enclosed in receptacle.
Hips: Globular; with inconspicuous neck; smooth; walls of medium thickness. Color—green.
Sepals: Permanent; moderately long in relation to size of flower and hip; spear-shaped.
Seeds: Medium number; small.

*Plant*

Foliage:

*Leaves.*—Compound of 7 leaflets; normal abundance; moderately small; very glossy.

*Leaflets.*—Shape—ovoid. Apex—acute. Base—obtuse. Margin—simply serrate.

*Color.*—Mature: upper surface—Spinach Green, Plate 0960; under surface—Fern Green, Plate 0862. Young: upper surface—near Lettuce Green, Plate 861; under surface—near Fern Green, Plate 0862, lightly overlaid on margins with maroon.

*Rachis (the supporting stem of the compound leaf).*—Light. Upper side—grooved; edges lined with gland-tipped hairs. Under side—sparsely prickly.

*Stipules.*—Moderately long; medium width; with very short points turning out at an angle of more or less 45°.

*Disease resistance.*—Resistant to mildew and blackspot; comparable to that of the average rose variety grown under the same cultural conditions at West Grove, Pennsylvania.

Growth:

*Habit.*—Bushy; trailing; much-branched.

*Growth.*—Free.

*Canes.*—Medium caliper.

*Main stems.*—Bright. Color—Lettuce Green, Plate 861/1. Prickles—many, pointed downwards; color—brown. Hairs—none.

*Branches.*—Bright. Color—Lettuce Green, Plate 861/1. Prickles—many; pointed downwards. Hairs—none.

*New shoots.*—Bright. Color—Pod Green, Plate 061, often with a reddish overlay on one side of shoot. Prickles—many; color—reddish. Hairs—none.

I claim:

A new and distinctive variety of rose plant of the shrub class, substantially as herein shown and described, characterized particularly as to novelty by the unique combination of a compact and bushy plant habit, with a gradually spreading habit which makes the plant suitable for hedge or ground cover purposes, glossy, disease resistant foliage, outstandingly good floriferousness and continuity of flowering, a habit of bearing the flowers in clusters, a distinctive and attractive white flower color, a slight, spicy flower fragrance, and a superior winter hardiness.

No references cited.